(12) United States Patent
Loescher et al.

(10) Patent No.: US 8,424,519 B2
(45) Date of Patent: Apr. 23, 2013

(54) POSITIVE AIRWAY PRESSURE APPARATUS

(75) Inventors: Thomas C. Loescher, Rancho Santa Fe, CA (US); Dennis L. Fitzwater, Strawberry, AZ (US)

(73) Assignee: A Plus Medical, Carlsbad, CA (US)

( * ) Notice: Subject to any disclaimer, the term of this patent is extended or adjusted under 35 U.S.C. 154(b) by 586 days.

(21) Appl. No.: 12/770,038

(22) Filed: Apr. 29, 2010

(65) Prior Publication Data

US 2010/0282256 A1 Nov. 11, 2010

Related U.S. Application Data

(60) Provisional application No. 61/175,962, filed on May 6, 2009.

(51) Int. Cl.
*A61M 11/00* (2006.01)
(52) U.S. Cl.
USPC ............................... 128/203.16; 128/204.18
(58) Field of Classification Search ............. 128/203.16, 128/200.29, 202.27, 204.16, 204.18, 205.12, 128/205.23, 203.27, 205.28, 206.11, 207.18; 141/285, 286
See application file for complete search history.

(56) References Cited

U.S. PATENT DOCUMENTS

| 4,253,501 | A | * | 3/1981 | Ogle ............................ 141/27 |
| 7,077,154 | B2 | | 7/2006 | Jacobs et al. |
| 7,604,004 | B2 | * | 10/2009 | Jagger et al. ............. 128/201.12 |
| 2005/0072470 | A1 | | 4/2005 | Jacobs et al. |
| 2009/0056719 | A1 | | 3/2009 | Newman, Jr. |

FOREIGN PATENT DOCUMENTS

| EP | 1 084 727 A2 | 3/2001 |
| FR | 2 158 603 | 6/1973 |

OTHER PUBLICATIONS

International Search Report and Written Opinion for International Application No. PCT/US2010/033172 filed Apr. 30, 2010.

* cited by examiner

*Primary Examiner* — Steven Douglas
(74) *Attorney, Agent, or Firm* — Knobbe, Martens, Olson & Bear, LLP

(57) ABSTRACT

An apparatus configured to provide positive airway pressure in a respiratory circuit comprises a container configured to be filled to a preselected level with liquids; a drop tube assembly comprising a hollow gas tube rotatably mounted in said container having an upper end extending a static distance outwardly of the container and connected to a respiratory circuit downstream of a user, and a hollow drop tube reciprocally movable upwardly and downwardly in the liquid in response to rotational movement of the gas tube. The container is provided with a gas vent and a liquid fill port.

20 Claims, 9 Drawing Sheets

POSITIVE AIRWAY PRESSURE APPARATUS

CROSS REFERENCE TO RELATED APPLICATION

This application claims priority to U.S. Provisional Application No. 61/175,962 filed May 6, 2009, the entirety of which is hereby incorporated by reference.

BACKGROUND OF THE INVENTION

Various methods and devices have been proposed for achieving positive airway pressure (PAP) for continuous positive airway pressure (CPAP), expiratory positive airway pressure (EPAP) and positive expiratory pressure (PEP) or positive end expiratory pressure (PEEP). Such techniques are used to enhance bronchial hygiene therapy by providing above atmospheric pressure at the airway during expiration (PEEP, PEP and EPAP) or continuously throughout the expiratory and inspiratory cycles (CPAP). Such techniques change the baseline pressure to aid in oxygenation by preventing collapse of unstable alveolar units due to lack of surfactant or disease, and maintain the alveoli open and restore functional residual capacity (FRC) of the patient.

A number of methods and apparatus for creating positive airway pressure have been used, including spring-loaded PEEP valves, magnetic valves, inflatable balloon threshold resistors and Venturi threshold resistors. An underwater or water seal PEEP valve uses fewer mechanical components, and is a practical, efficient and relatively inexpensive apparatus for adequately achieving the desired positive airway pressure. Such an apparatus is well known in the prior art, and described, for example, in U.S. Pat. No. 7,077,154, the description of which is incorporated herein by reference.

In the aforesaid patent, a drop tube is positionable at various discreet positions ensuring accurate depth and stability of the tube at the desired depth in the fluid. Although the design of the aforesaid disclosed apparatus is intended to ensure the secure positioning of the drop tube in the liquid at the desired depth, it does so at the expense of requiring various lengths of the elongated drop tube to extend upwardly out from the lid of the apparatus and is inconvenient to adjust.

SUMMARY OF THE INVENTION

The apparatus described herein is configured to provide positive airway pressure in a respiratory circuit and comprises a container for holding a volume of liquid, and a drop tube assembly comprising a first hollow tube or pipe (gas tube) rotatably mounted in the container, the first tube having an upper end extending outwardly from the container at a static distance and connected to expiratory tubing of a respiratory circuit, and a second hollow tube or pipe (drop tube) reciprocally movable upwardly and downwardly relative to the water level in response to rotational movement of the first hollow tube. In one embodiment, the apparatus includes a guide member to assist in guiding the reciprocal drop tube travel. The container also includes a gas vent orifice above the liquid level. The design of the drop tube assembly allows the drop tube to be moved to preselected, discreet and secured positions below the liquid level by simple incremental rotation of the gas tube. The specific designs and alternate embodiments of the apparatus will be described further hereinafter in the detailed description.

DETAILED DESCRIPTION

Figure 1:
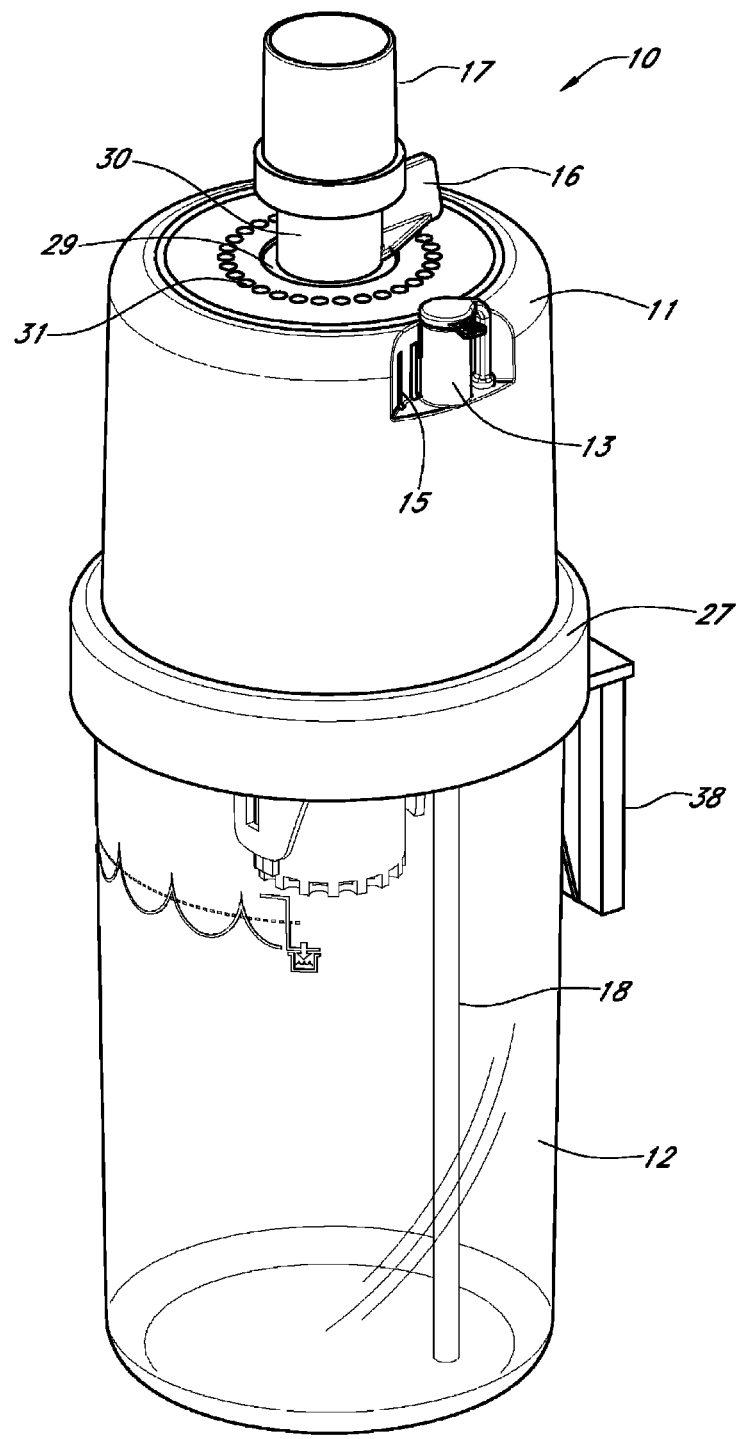
FIG. 1 is a perspective view of the assembled apparatus.
Figure 2:
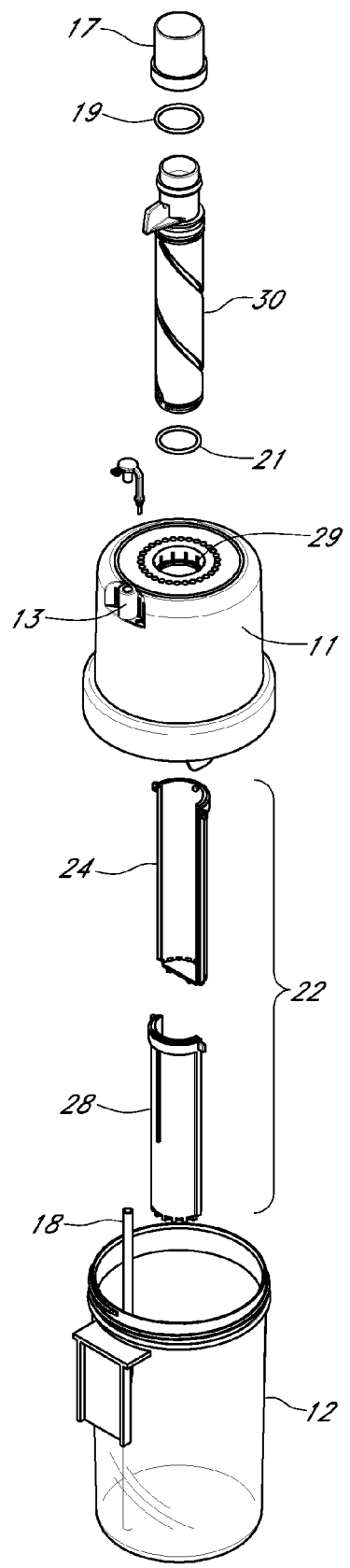
FIG. 2 is an exploded view of the apparatus.
Figure 3:
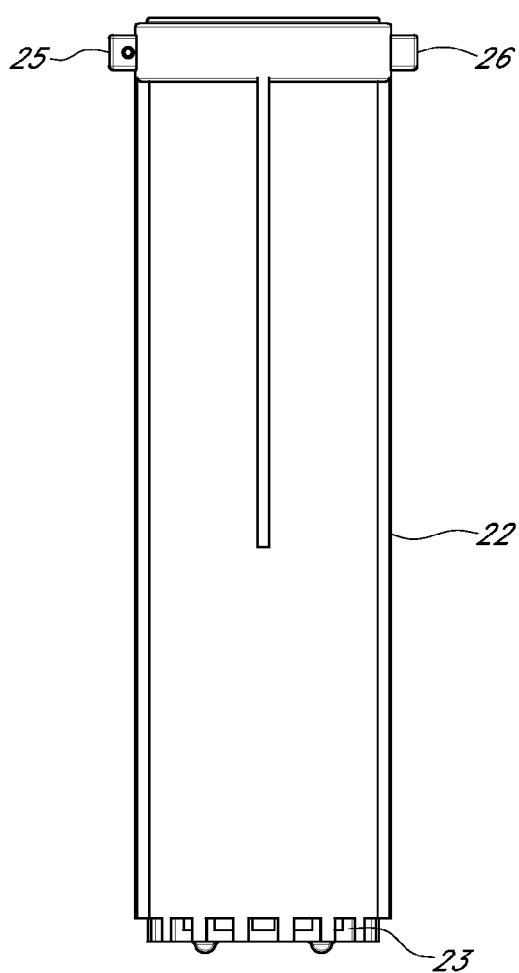
FIG. 3 is a side view of the drop tube of the assembly.
Figure 4:
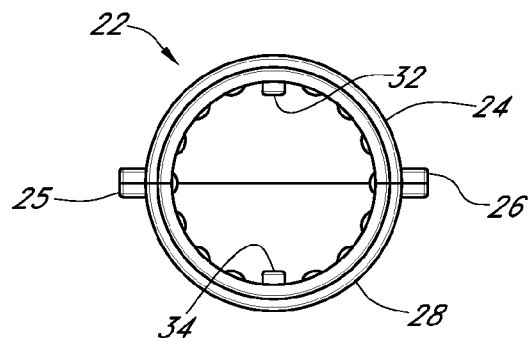
FIGS. 4 and 5 are top and bottom plan views of the drop tube of FIG. 3.
Figure 5:
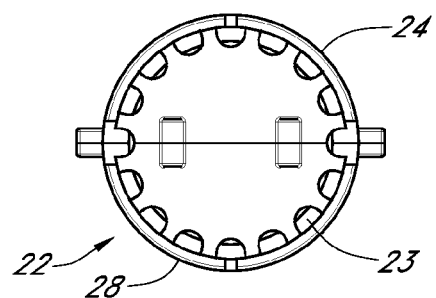
Figure 6:
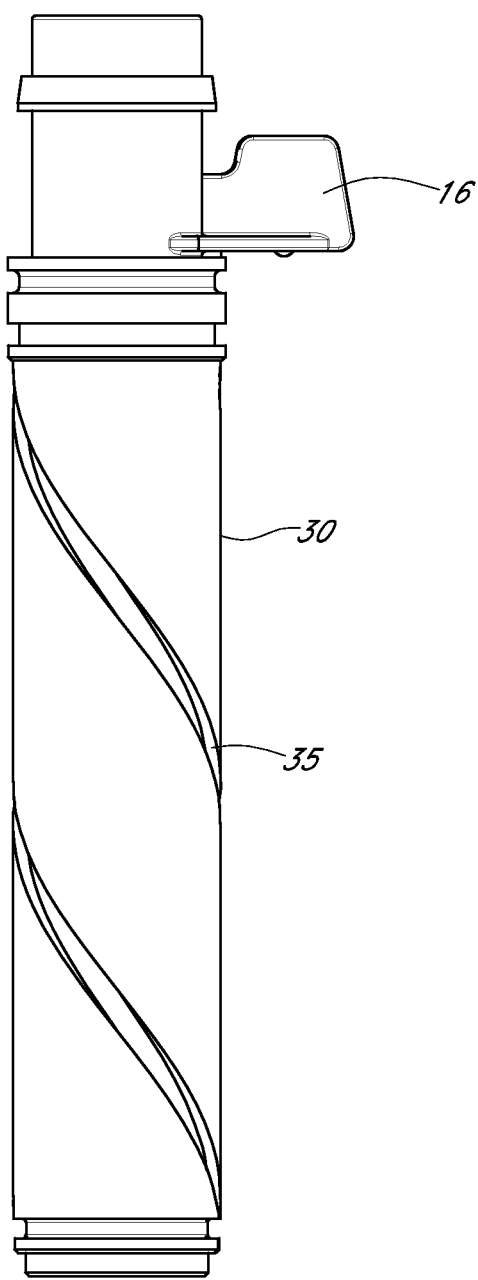
FIG. 6 is a side view of the rotatable gas tube.

The exterior components and features of the assembled apparatus 10 shown in FIG. 1 include a cap 11 having an opening 29 at the upper surface through which extends a rotatable gas tube 30. At the upper end of the gas tube is mounted a swivel adapter which serves as the gas inlet connector for expiratory tubing of a respiratory circuit (not shown). Also formed in the cap 11 is a water adjustment port 13 which is connected to a water adjustment feed tube 18. This port and tube allow a user to introduce water into the water reservoir or jar 12 to the desired volume. Also formed on the cap 11 are one or more gas outlet ports 15 which allow gas introduced into the apparatus from the expiratory tubing of a respiratory circuit to be vented from the jar to the atmosphere. The cap 11 also preferably includes a collar 27 which is interiorly threaded to engage threads formed on the upper end of jar 12, whereby the cap can be screwed on and off for assembly, cleaning or otherwise affording access to the interior of the jar as well as the interior assembly components. Alternatively, the cap may be snap-fit on the jar, or may be permanently secured, for example, by gluing or ultrasonic welding. A bracket 38 is also preferably formed on the exterior of the jar, whereby the assembly can be mounted on gas delivery equipment. Gas tube 30 extends upwardly out of opening 29 on the top of cap 11. A swivel adapter 17 is mounted at the upper end of the gas tube 30 for securing expiratory tubing of a respiratory circuit. A gas seal is provided by O-ring 19 (FIG. 2). As previously noted, water adjustment tube 18 extends into the reservoir of jar 12, with its upper end communicating with the water adjustment port 13.

As shown in FIG. 2, the drop tube assembly of the apparatus includes the rotatable gas tube 30 and drop tube 22. Preferably, both of these tubes are hollow and cylindrical. The drop tube 22 preferably comprises two half sections 24 and 28. The two sections may be joined by any convenient means, such as adhesive or other bonding means, or many components for being snap-fit together. Alternatively, drop tube 22 may be molded as a single component.

Embodiments of the drop tube assembly components are illustrated in FIGS. 3-6 with guide teeth or followers 32, 34 formed on the interior of drop tube 22 for being received in helical track 35 formed on the exterior of cylindrical gas tube 30. As the gas tube is rotated, the guide teeth provide for selective upward and downward movement of the drop tube. The operation of this assembly is further illustrated in FIGS. 8 and 9 where it is observed that the guide teeth 32 and 34 slidably engage the helical track 35.

Figure 7:
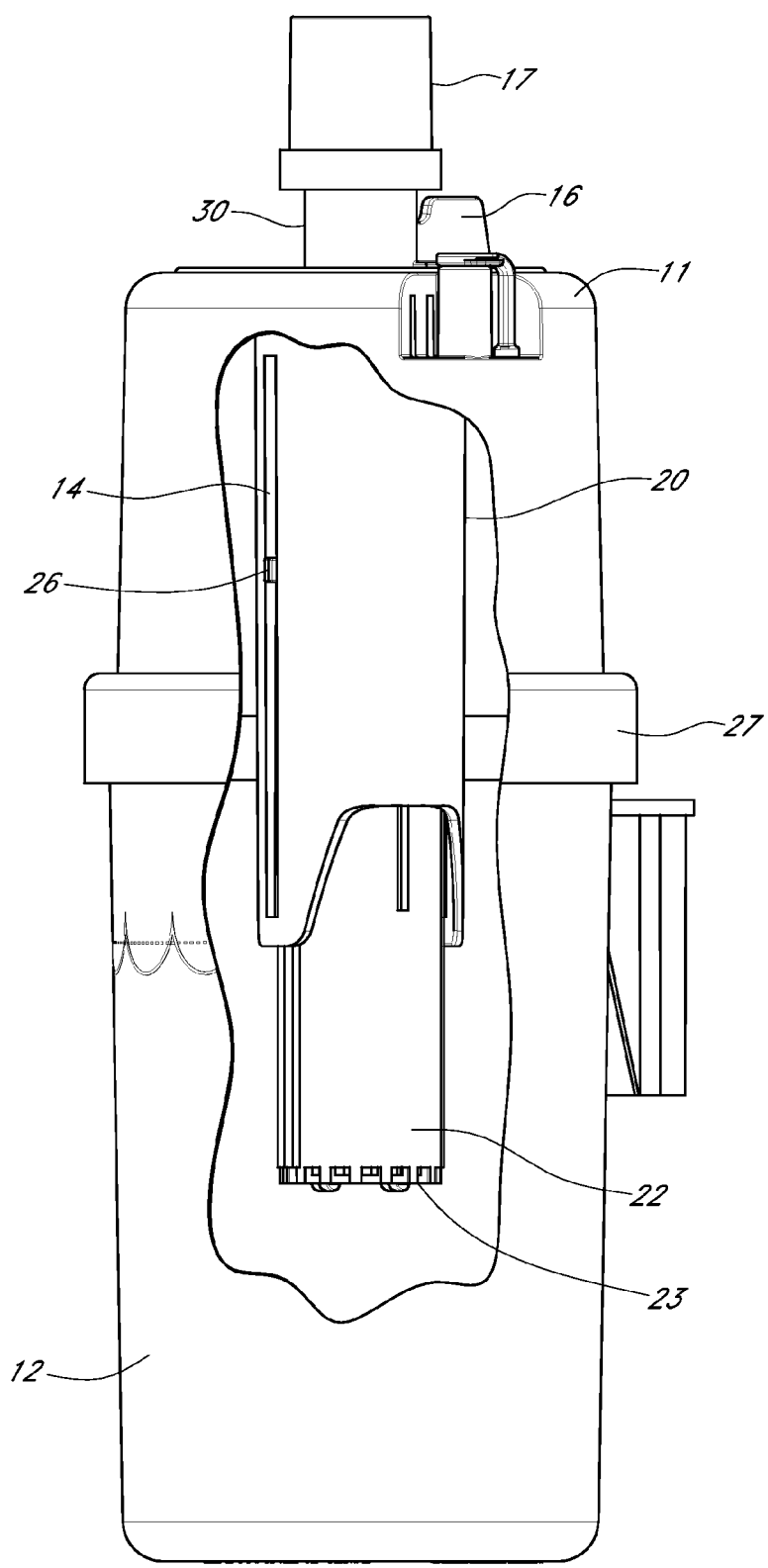
FIG. 7 is a side view of the apparatus assembly with the exterior partially cut away to show the interior assembly components.
Figure 8:
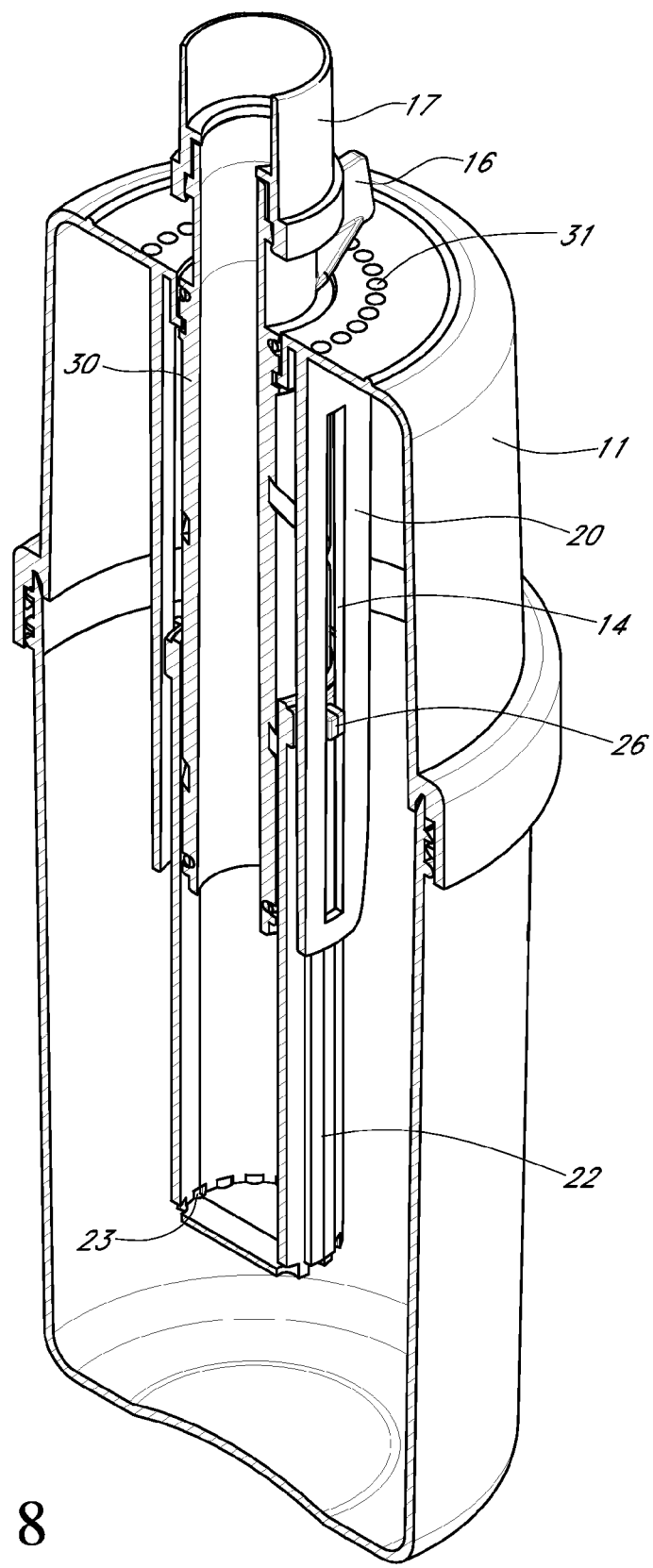
FIG. 8 is a side sectional view showing the internal components and design of the drop tube assembly.
Figure 9:
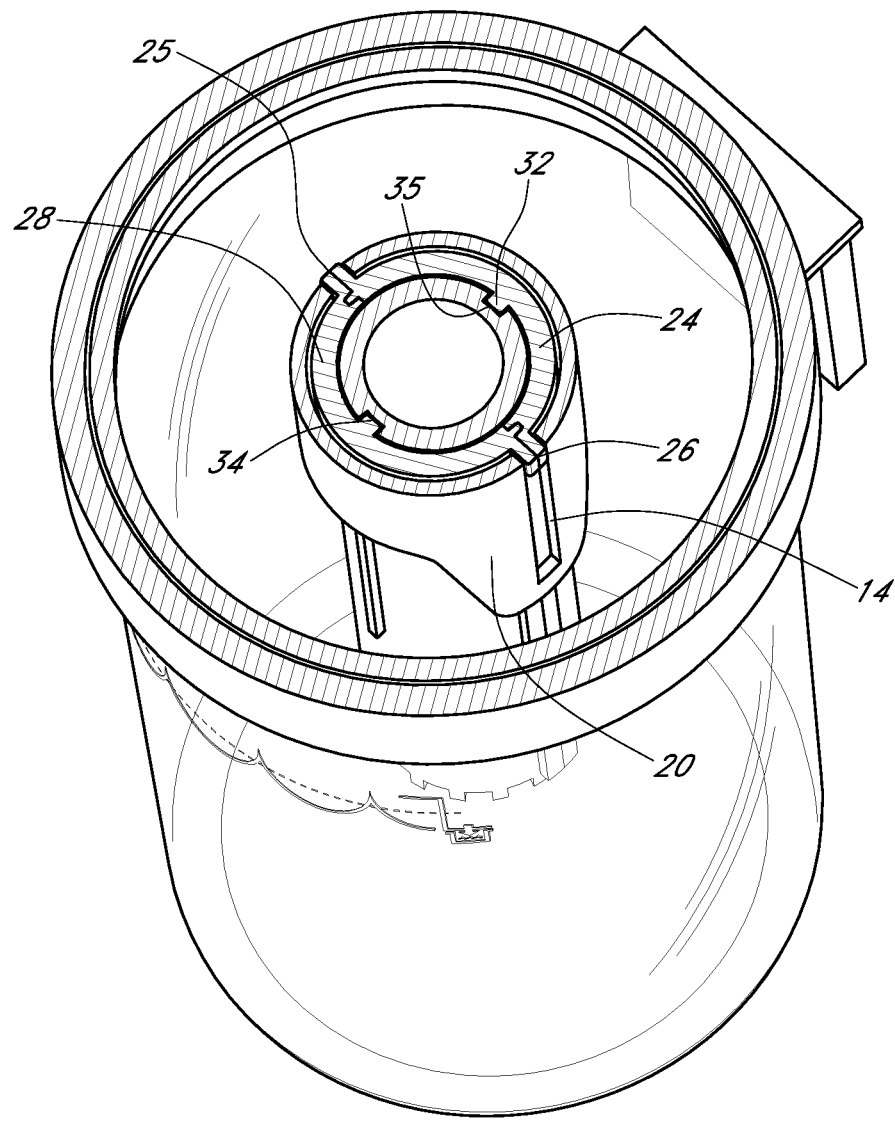
FIG. 9 is a sectional perspective view from the top of the drop tube assembly.

Also referring to FIGS. 7 and 8, the upward and downward movement of drop tube 22 is further enabled by slot lugs 25, 26 which project outwardly from drop tube 22 and which are slidably received in guide slot 14 formed on guide sleeve 20 which extends vertically and downwardly into the apparatus jar. A guide member in the form of a guide sleeve 20 is preferably formed on or otherwise secured to the interior surface of cap 11. The guide sleeve preferably includes at least two opposite guide slots 14 for slidably engaging the guide lugs or protuberances projecting outwardly from opposite sides of the cylindrical drop tube 22. Thus, the guide sleeve is stationary and the cooperation of the slot lugs allow vertical movement of the drop tube but prevent rotational movement of the drop tube in response to rotation of the gas tube 30.

In the embodiment illustrated, the diameter of the cylindrical gas tube is smaller than the diameter of the cylindrical drop tube 22, and the guide sleeve 20 is of a greater diameter than the drop tube 22. However, it should be appreciated that the guide sleeve 20 need not be cylindrical, and may be of other designs, such as elongated downwardly extending slotted arms or equivalent members, so long as the slots, preferably two or more, are provided to cooperate with the slot lugs or other protuberances formed on the drop tube to prevent rotation of the drop tube, but allow for its reciprocal vertical upward and downward movement in response to rotation of the gas tube.

Alternatively, in an embodiment not shown, the drop tube may be positioned interiorly of the gas tube, and the helical track cooperating with the drop tube may be formed on the interior surface of the gas tube. In such an embodiment, the vertical guide sleeve may be in the form of arms extending downwardly and fixed stationary on the lid and extend downwardly into the interior of the hollow drop tube. Moreover, the cooperating components of the guide member with the drop tube may be modified from those previously described whereby the drop tube is provided with a slot for engaging protuberances extending from the guide member. Thus, so long as the guide member and the drop tube have cooperating components which prevent rotation of the drop tube in response to rotation of the gas tube and yet provide for the upward and downward movement of the drop tube in response to rotation of the gas tube, the desired operation of the apparatus within the purview of the invention described herein is achieved.

In yet another embodiment, not illustrated, a guide member or members may be formed and extend vertically upwardly from the base of the reservoir or jar, and which guide member or members will cooperate with a drop tube to prevent its rotational movement, and yet provide for its reciprocal upward and downward movement in response to rotation of the gas tube.

Regardless of which of the aforesaid embodiments are incorporated in the design of the apparatus, a beneficial design feature of the apparatus is in providing for upward and downward selective reciprocal movement of the drop tube without changing the length of the guide tube or gas tube which extends outwardly of the apparatus. Thus, because of the unique design of the apparatus as described hereinabove, the drop tube may be introduced into the liquid in the reservoir at any desired level to achieve the desired positive airway pressure in the respiratory circuit without extending the drop tube or the gas tube at greater lengths or distances from the apparatus, but instead extends outwardly at a static distance throughout the operation of the apparatus, regardless of how far the drop tube is introduced into the reservoir.

In another embodiment as shown in FIGS. 3, 5, 7 and 8, the lower end of drop tube 22 is provided with a plurality of orifices in the form of gas diffusing ports 23 through which gas from the expiratory limb of a respiratory circuit directed into drop tube 23 via swivel adapter 17 and gas tube 30 is diffused into the reservoir 12. Any number of the plurality of gas diffusing ports may be used, the intention being to evenly distribute into the liquid in the reservoir without creating large bubbles and/or uneven or irregular bubbling. The advantage of the plurality of gas diffusing ports is to achieve relatively smaller bubbles, and thereby a steady, regular and quiet flow of the gas in the liquid, and to maintain a more accurate and steady backpressure. This feature is especially important at relatively low gas flows (1 to 12 LPM) at pressure ranges of 1 to 10.0 cm $H_2O$. Such accuracy is especially advantageous when the device is used with neonatal, newborn and infant patients in acute hospital critical-care facilities to evaluate end expiratory lung pressure in the aforesaid constant gas flows and pressures.

Figure 10:
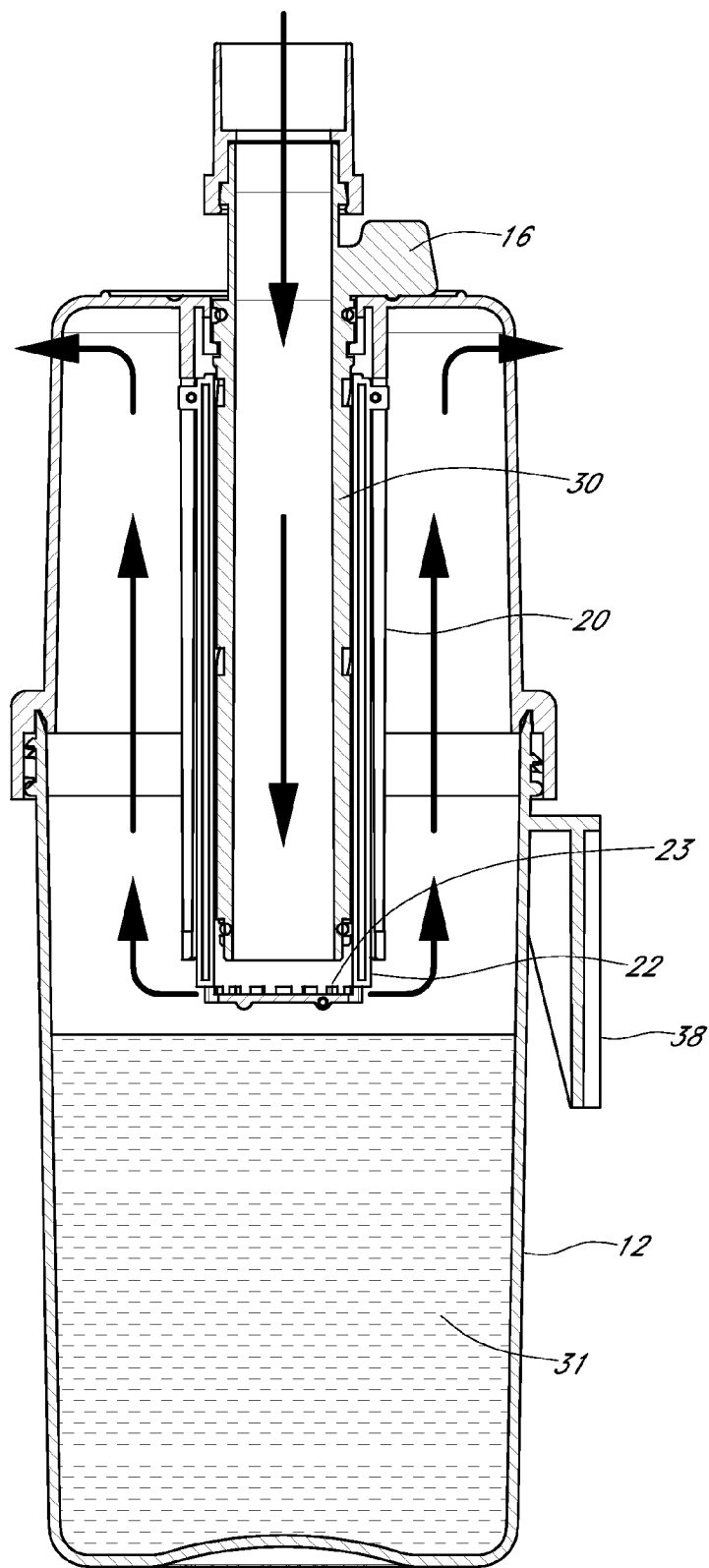
FIGS. 10 and 11 illustrate features of the apparatus with the drop tube fully retracted and fully extended, respectively.
Figure 11:
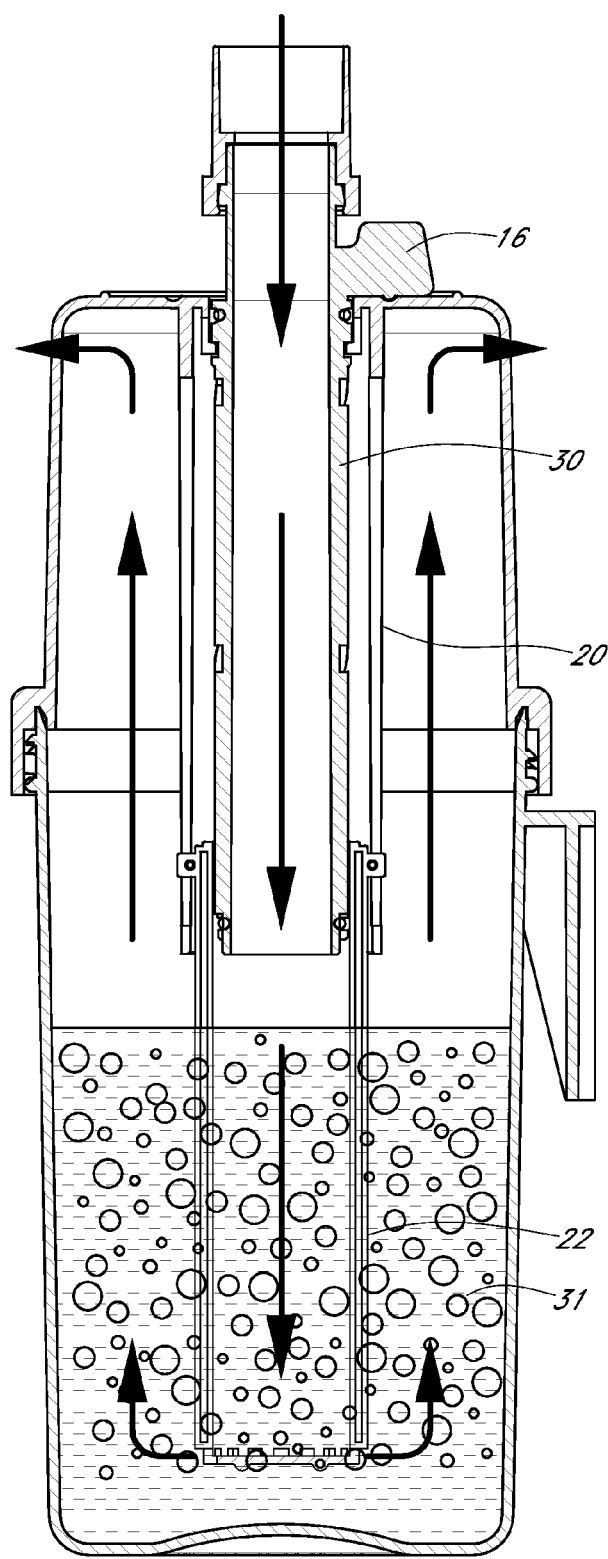

Referring also to FIGS. 10 and 11, in FIG. 10 there is illustrated the positive airway pressure apparatus with the drop tube at its uppermost position above the surface of liquid 31 present in reservoir 12. Gas flowing through the gas tube 30 is diffused at the lower end of the drop tube 22 via gas diffusing ports 23. In such a position, the backpressure is at minimum since the lower end of the drop tube is not immersed into the liquid. In FIG. 11, the drop tube 22 is shown in its lowermost position, which has been achieved by an operator or user rotating the gas tube 30 via lever 16 secured adjacent to the upper end of the gas tube and the upper cap surface. It is observed that a plurality of evenly spaced and dispersed bubbles are created and passed through the liquid 31. The operator may readily position the drop tube to any desired distance into the liquid to achieve the desired backpressure, again, by simply rotating the lever 16, which action causes rotation of the gas tube and results in the upward or downward movement of the drop tube. It will be noted by comparing FIGS. 9 and 10, regardless of the fully retracted or fully extended drop tube position, the upper end of the gas tube and the swivel adapter which is connected to the expiratory limb of the respiratory circuit is fixed relative to the distance it extends outwardly above the cap of the apparatus. Thus, adjustment of the backpressure is readily made without disturbing the tubing which directs the gas flow to the apparatus via the expiratory circuit, making the apparatus efficient and easy to use at or near the bedside in a respiratory care environment.

Referring again to FIGS. 1 and 8, in another embodiment, the upper surface of cap 11 may be provided with indicia 31 in any suitable form, for example, a plurality of detents, nubs or markings, cooperating with the lever 16 to display or otherwise indicate the extent of rotation of the gas tube may also secure the position of the lever. Such indicia, markings or other such features are advantageously located to coordinate the position of the lever with the depth of the end of the drop tube into the liquid. With such an arrangement, the operator may turn the lever 16 to the position that shows and yields the submersion of the drop tube into the liquid to achieve the desired backpressure.

The apparatus described herein is typically used with a respiratory circuit configured to direct breathable gas to a patient via inspiratory tubing and a mask, nasal cannula or mouthpiece, and expiratory tubing for directing expired gas from the patient to the positive airway pressure apparatus.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. An apparatus for providing positive airway pressure in a respiratory circuit comprising:
   a container for holding a volume of liquid; and
   a drop tube assembly configured for directing gas from a respiratory circuit to said container comprising:
      a first tube having an upper gas inlet end and a lower gas outlet end, said first tube rotatably mounted in said container and extending downwardly therein with said upper gas inlet end extending a static distance outwardly therefrom, and
      a second tube coaxially mounted along said first tube and movable upwardly and downwardly therealong in response to rotation of said first tube.

2. The apparatus of claim 1 wherein said drop tube assembly comprises helical track means for moving said second tube upwardly and downwardly along said first tube in response to rotation of said first tube.

3. The apparatus of claim 1 wherein said container includes a guide member secured therein and cooperating with said drop tube assembly for guiding said second tube.

4. The apparatus of claim 3 wherein said guide member includes one or more guide slots and said second tube includes one or more components thereon received in said one or more guide slots, respectively.

5. The apparatus of claim 3 wherein said second tube comprises one or more first guide components thereon cooperating with said guide member and one or more second guide components thereon cooperating with said first tube.

6. The apparatus of claim 5 wherein said second tube is mounted to move upwardly and downwardly along the outside of said first tube, wherein said guide member extends along the outside of said second tube, and wherein said second tube engages said first tube and said guide member.

7. The apparatus of claim 5 wherein said guide member comprises one or more guide slots thereon cooperating with said one or more first guide components, respectively, and wherein said first tube comprises a helical track cooperating with said one or more second guide components, respectively.

8. The apparatus of claim 1 wherein said container includes a cap having a port through which the upper gas inlet end of said first tube extends and wherein said guide member is secured adjacent to said port and extends downwardly therefrom in said container.

9. The apparatus of claim 1 wherein said second tube has a plurality of gas diffusing ports adjacent to said lower gas outlet end.

10. The apparatus of claim 1 wherein said drop tube assembly is configured to provide selected distance of upward/downward movement of said second tube in response to a selected rotational movement of said first tube.

11. The apparatus of claim 10 wherein said cap includes indicia cooperating with said component for showing the amount of rotation of said first tube.

12. A respiratory circuit comprising an expiratory tubing extending from a patient to a positive airway pressure apparatus, said apparatus comprising:
    a container filled to a preselected level with liquid;
    a drop tube assembly comprising a gas tube rotatably mounted in said container having an upper end extending outwardly a static distance of said container and connected to said expiratory tubing, and a drop tube coaxially mounted along said gas tube and reciprocally movable upwardly and downwardly relative to said water level in response to rotational movement of said gas tube, and
    a gas vent orifice in said container above said liquid level.

13. The apparatus of claim 12 wherein said drop tube assembly is configured to provide selected distance of upward/downward movement of said drop tube in response to a selected rotational movement of said gas tube.

14. The apparatus of claim 12 including markings on said container cooperating with said upper end of said gas tube for showing the rotational movement thereof of said gas tube.

15. The apparatus of claim 12 wherein said drop tube comprises a lower end having a plurality of gas diffusing orifices.

16. The apparatus of claim 12 wherein said drop tube assembly comprises a helical track configured to provide the upward/downward movement of said drop tube in response to rotational movement of said gas tube.

17. The apparatus of claim 16 wherein said helical track extends along said gas tube.

18. The apparatus of claim 17 wherein said drop tube includes one or more followers received in said helical track.

19. The apparatus of claim 18 wherein said container includes a stationary guide member having one or more guide slots therein and wherein said drop tube includes one or more components cooperating with said one or more guide slots, respectively.

20. The apparatus of claim 16 wherein said gas tube and said drop tube are cylindrical, said drop tube has a diameter larger than said gas tube and moves upwardly and downwardly along the exterior thereof.

* * * * *